(12) United States Patent
De Salvo et al.

(10) Patent No.: US 12,039,879 B2
(45) Date of Patent: Jul. 16, 2024

(54) ELECTRONIC DEVICE AND METHOD FOR EYE-CONTACT TRAINING

(71) Applicant: YOUR SPEECH FACTORY AB, Malmo (SE)

(72) Inventors: Vincenzo De Salvo, Malmö (SE); Simone Frattasi, Fredriksberg (DK)

(73) Assignee: YOUR SPEECH FACTORY AB, Malmo (SE)

( * ) Notice: Subject to any disclaimer, the term of this patent is extended or adjusted under 35 U.S.C. 154(b) by 195 days.

(21) Appl. No.: 17/629,074

(22) PCT Filed: Aug. 21, 2020

(86) PCT No.: PCT/SE2020/050809
§ 371 (c)(1),
(2) Date: Jan. 21, 2022

(87) PCT Pub. No.: WO2021/040602
PCT Pub. Date: Mar. 4, 2021

(65) Prior Publication Data
US 2022/0246060 A1    Aug. 4, 2022

(30) Foreign Application Priority Data
Aug. 23, 2019   (SE) .................... 1950971-0

(51) Int. Cl.
*G09B 19/04* (2006.01)
*G06F 3/01* (2006.01)
(Continued)

(52) U.S. Cl.
CPC .............. *G09B 19/04* (2013.01); *G06F 3/013* (2013.01); *G06V 40/18* (2022.01); *G10L 25/48* (2013.01)

(58) Field of Classification Search
CPC .......... G09B 19/00; G09B 19/04; G06F 3/013; G10L 25/48; G06V 40/18
See application file for complete search history.

(56) References Cited

U.S. PATENT DOCUMENTS 10,113,877 B1  10/2018  Schaefer
10,275,023 B2   4/2019  McKenzie et al.
(Continued)

FOREIGN PATENT DOCUMENTS

JP    2018180503 A    11/2018
KR    101563312 B1    10/2015
(Continued)

OTHER PUBLICATIONS

Swedish Office Action from corresponding Swedish Application No. 1950971-0, dated Jan. 18, 2022, 5 pages.
(Continued)

*Primary Examiner* — Timothy A Musselman
(74) *Attorney, Agent, or Firm* — Tucker Ellis LLP

(57) ABSTRACT

The present disclosure relates to digital solutions for eye-contact training. According to a first aspect, the disclosure relates to a computer-implemented method for eye-contact training. The method comprises presenting S1, on the one or more displays, one or more user interface objects indicative of one or more desired gaze areas representing one or more spectators of a virtual audience of the user. The method further comprises obtaining S3, using the camera, eye-gaze data indicative of the user's actual gaze direction and evaluating S4 a level of eye contact between the user and the virtual audience based on one or more rules defining a level of eye contact. The method also comprises providing S5 user feedback indicative of the evaluated level of eye-contact to
(Continued)

the user. The disclosure also relates to an electronic user device and to a computer program configured to perform the method.

21 Claims, 8 Drawing Sheets

(51) Int. Cl.
*G06V 40/18* (2022.01)
*G10L 25/48* (2013.01)

(56) References Cited

U.S. PATENT DOCUMENTS

| 10,446,055 | B2* | 10/2019 | Gupta | G09B 9/00 |
|---|---|---|---|---|
| 2012/0290401 | A1 | 11/2012 | Neven | |
| 2014/0198189 | A1 | 7/2014 | Aronsson et al. | |
| 2015/0131055 | A1 | 5/2015 | Catanzariti et al. | |
| 2015/0223731 | A1 | 8/2015 | Sahin | |
| 2015/0310657 | A1 | 10/2015 | Eden | |
| 2016/0019801 | A1 | 1/2016 | Feerst | |
| 2016/0080874 | A1 | 3/2016 | Fullam | |
| 2018/0270571 | A1 | 9/2018 | Di Censo et al. | |

FOREIGN PATENT DOCUMENTS

| KR | 20190048144 A | 5/2019 |
|---|---|---|
| WO | 2015114824 A1 | 8/2015 |
| WO | 2015125243 A1 | 8/2015 |
| WO | 2016142933 A1 | 9/2016 |
| WO | 2019098450 A1 | 5/2019 |

OTHER PUBLICATIONS

International Search Report from corresponding International Application No. PCT/SE2020/050809, dated Sep. 30, 2020, 5 pages.
Supplementary European Search Report and Search Opinion from corresponding European Application No. 20858210, dated Jul. 3, 2023, 7 pages.

* cited by examiner

ELECTRONIC DEVICE AND METHOD FOR EYE-CONTACT TRAINING

TECHNICAL FIELD

The present disclosure relates to the area of eye tracking and more specifically to digital solutions for conducting the gaze of a user to different desired areas on one or more displays for training eye-contact. The disclosure also relates to an electronic user device and to a computer program configured to perform the method.

BACKGROUND

It is known to use eye tracking systems that can measure a computer user's eye activity to determine the location at which the user's eyes are focused (that is a user's "gaze"). For instance, certain eye tracking systems can determine the location at which a user's eyes are focused on a display device. This information can then be used for various purposes, such as selecting a user interface ("UI") window that should receive UI focus (i.e. receive user input) based upon the location of the user's gaze.

However, in some situations it may be desirable to not only trace the user's gaze but to also direct the user's gaze to a certain location on a display at which a user is looking. This may be beneficial in several different situations. One example situation is in eye-contact training, where conducting of a user's gaze may be a helpful tool to improve public speaking skills. Fear of public speaking is among the top fears in the world. Thus, it may be desirable to introduce digital solutions that aids a user to gaze in a desired direction while practicing speaking to become a good presenter, both in live situations and in online meetings. Thereby, it may be possible for people training for a presentation or a pitch to become more confident and competent speakers.

SUMMARY

It is an object to provide a way of conducting a user's gaze on a display. Furthermore, it is an object, to provide a simple way of eye contact training by guiding a user's gaze on a display.

According to a first aspect, the disclosure relates to a computer-implemented method for eye-contact training. The method comprises presenting, on the one or more displays, one or more user interface objects indicative of one or more desired gaze areas representing one or more spectators of a virtual audience of the user. The method further comprises obtaining, using the camera, eye-gaze data indicative of the user's actual gaze direction and evaluating a level of eye contact between the user and the virtual audience based on one or more rules defining a level of eye contact, by analysing an extent to which the user's actual gaze direction indicated by the eye-gaze data corresponds to the one or more desired gaze areas representing the one or more spectators. The method also comprises providing user feedback indicative of the evaluated level of eye-contact to the user. With the proposed technique, it is possible, to, based on a user's present gaze direction, guide the user to look at a desired part of the display or at an object or area outside the display. Hence, the user may be trained to move his/her gaze in a way that corresponds to "good" eye contact.

In some embodiments, the one or more rules comprises a minimum and/or maximum time the user's gaze direction should constantly remain on a gaze area indicated by a user interface object representing one of the spectators. This is one way of evaluating a level of eye-contact. In some embodiments, the minimum time corresponds to an estimated time it takes for the user to say at least one sentence.

In some embodiments, the rules are based on a timing within a speech to be performed by a user. Hence, the evaluation may be adapted to the speech.

In some embodiments, the presenting comprises presenting speech information related to a speech to be performed by the user, and wherein the rules are based on the speech information. Hence, eye-contact may be adapted to the content of a speech.

In some embodiments, the rules are based on phrases or tags in the speech information. Thereby, the user is trained to establish eye-contact at important parts of a speech.

In some embodiments, the method comprises continually repeating the presenting, the obtaining and the evaluating and providing the user-feedback indicative of the evaluated level of eye-contact to the user in real-time. Hence, feedback is given in real time, e.g. while performing the training by running a software application on the electronic user device or even during a "live" speech.

In some embodiments, the one or more user interface objects comprises a plurality user interface objects positioned on distinct parts of the one or more displays and representing individual spectators, and wherein the method comprises moving the desired gaze area between the one or more gaze areas, according to a pre-defined eye contact training pattern. Hence, the user may be trained to look at a particular user in a virtual audience.

In some embodiments, the method comprises continually indicating one spectator of the one or more of the spectators, with whom eye contact should be established and the evaluating comprises evaluating a level of eye contact between the user and the indicated spectator. Hence, the user may be trained to establish eye contact with individual users of a virtual audience.

In some embodiments, the one or more user interface objects comprises one single user interface object positioned right below the camera, wherein the single user interface object represents eye-contact via the camera. Thereby, it is possible to encourage the user to establish perceived eye-contact with the audience via the camera.

In some embodiments, the method further comprises recording a speech signal representing the user's speech, and wherein the evaluating is also based on a speech pattern of the recorded speech signal. Hence, the user may be trained to move his/her gaze in a way that matches his/her speech.

In some embodiments, the moving of the desired gaze area is performed in response to one or more triggers.

In some embodiments, the one or more triggers comprises one or more of a user input, expiry of a timer, and detection of a silent period in a recorded speech signal.

In some embodiments, the obtaining comprises estimating at least one of pupil centre, eye fixation time, eye glint data, pupil dilation and constriction, blink rates, and corneal reflection.

In some embodiments, the one or more desired gaze areas are positioned on the one or more displays or outside the one or more displays.

In some embodiments, the user-feedback comprises a visible, an audible or a tactile signal.

According to a second aspect, the disclosure relates to an electronic user device for tracing a user's gaze direction, the electronic user device comprising a control device, one or more displays and a camera. The control device is configured to perform the method according to the first aspect.

According to a third aspect, the disclosure relates to a computer program comprising instructions which, when the program is executed by a control device, cause the electronic user device to carry out the method as described herein.

According to a fourth aspect, the disclosure relates to a computer-readable medium comprising instructions which, when executed by a control device, cause the electronic user device to carry out the method as described herein.

DETAILED DESCRIPTION

This disclosure proposes an interactive user interface, UI, that aids a user to look in a desirable direction. The direction may be towards a user interface object on a display or to an object outside the one or more displays. The UI is adapted for eye contact training and thus aids the user to have a gaze direction, which corresponds to "good" eye contact. There are many scientific principles for evaluating "good" eye contact. For example, eye contact may be considered "good" if certain criteria are fulfilled. For example, the speaker should look at one person only in the audience for as long as the speaker shall say one or more sentences (e.g., 7.55 sec) without moving the eyes away from that person. When the one or more sentences are said, the speaker should move the eyes to another person in the audience while making a long pause (i.e., without saying any words for as long as 1-2 sec) and must then start speaking again using the same principle. The proposed method may be used in combination with any principle for "good" eye contact.

This disclosure also proposes a method where UI objects are presented on one or more displays. The UI objects indicate where the user should look, i.e. in a desired gaze direction. The user's gaze is then evaluated, and feedback is provided to the user to inform the user whether he or she is looking in the desired direction. The technique is for use to practice good eye contact during a performance such as a presentation or a speech, including both online and a "live" performances.

In other words, in some embodiments, this disclosure proposes a UI that enables training of eye contact by means of one or more UI objects (e.g., avatars) displayed on a display (e.g., laptop display), wherein said UI provide real-time feedback (i.e., guidance) to the user regarding how to gaze based on tracking the eyes of the user by one or more cameras.

The proposed technique will now be further described with reference to FIG. 1 to FIG. 6. The technique will herein be described in connection with eye-contact training. However, it must be appreciated that the technique may also be implemented in other situations as will be explained below.

Figure 1A:
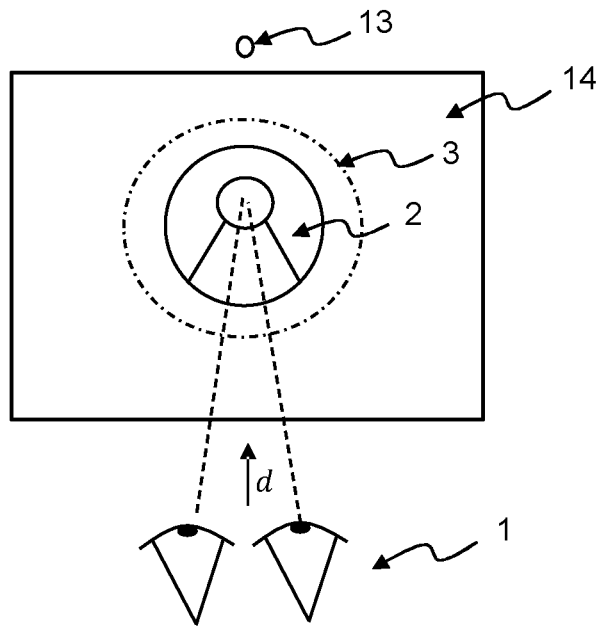
FIGS. 1a and 1b illustrate a user's gaze direction in relation to a UI object on a display.
Figure 1B:
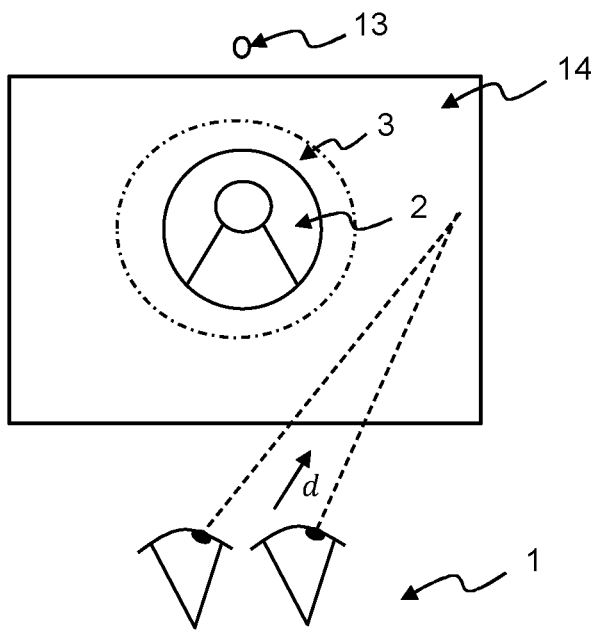

FIGS. 1a and 1b illustrate a user's gaze direction d in relation to a user interface, UI object 2 on a display 14. The UI object is indicative of a desired gaze area 3, i.e. a part at or outside the display where it is desirable that the user should look. In FIG. 1a the user 1 looks at a UI object 2, here illustrated as an avatar, that is presented on the display 14. In FIG. 1b the user 1 does not look at the UI object 2, but on another part of the display.

The user's eye gaze may be determined based on images captured by a camera 13 aiming at the user's face using known techniques e.g. revealed in patent application US2018081434 A1, which teaches techniques for detection of eye and head movement based on an image of a set of pupils. The gaze direction d may be defined in degrees in relation to a reference direction. The reference direction is e.g. a direction perpendicular to the display 14. Thus, by analysing the user's eye gaze, herein referred to as gaze direction, it is possible to determine (at least with a certain probability) that the user 1 is looking at a certain UI object 2.

In case of a video call or an online meeting it is typically important that the user strives at having good perceived eye contact with the other participants. This is typically achieved by looking into the camera 13, which is often located right above the screen 14. However, this kind of behaviour is not always intuitive. In such a scenario, it may therefore be desirable to analyse the user's gaze direction to determine whether the user looks into the camera 13 or not. A desired gaze 3 area would then be positioned around or at the camera 13. In other words, a determined gaze direction may be used to determine whether the user has good perceived eye-contact with the participants of an online session.

Figure 2A:
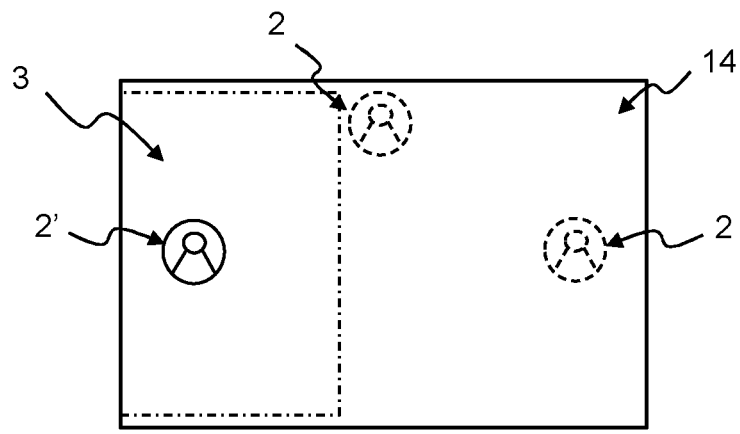
FIGS. 2a to 2c illustrate a display comprising UI objects representing different desired gaze areas according to one example embodiment.
Figure 2B:
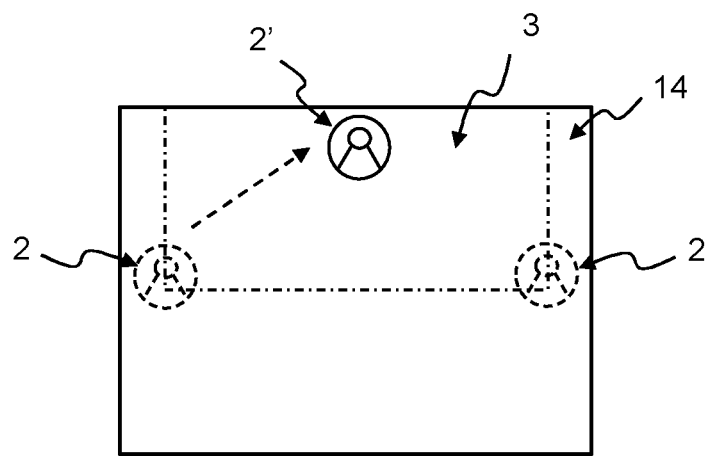
Figure 2C:
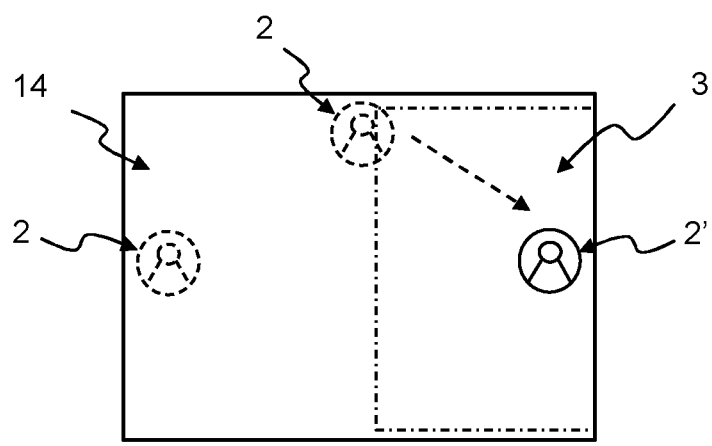

Eye-contact is also important in "live" scenarios, such as when a user is holding a speech for an audience comprising a plurality of people. Such a situation may be trained using the user interface illustrated in FIG. 2a-c. FIGS. 2a to 2c illustrate a display comprising UI objects 2 representing respective gaze areas 3 (indicated by dash-dotted contour) according to one example embodiment. FIG. 2a illustrates the gaze area 3 of the UI object 2 to the left (indicated by a solid border and a hyphen). FIG. 2b illustrates the gaze area 3 of the UI object 2 in the middle (indicated by a solid border and a hyphen). FIG. 2c illustrates the gaze area 3 of the UI object 2 to the right (indicated by a solid border and a hyphen). The UI objects 2 are avatars of spectators of a virtual audience of the user. This user interface may aid the user to train a speech that shall later be held for a "live" audience. Each avatar is associated with a respective gaze area 3. The gaze areas are used to evaluate whether a user is looking at the corresponding UI object 2. On a small display the gaze areas may be overlapping, as in FIGS. 2a to 2c.

When giving a speech it is typically desirable to let the user's gaze wander between the spectators in the audience. This may be practiced using the proposed UI. In the illustrated example, the presented UI objects are spectators of a virtual audience. In order to practice eye contact, the user may then be guided to look at one of the spectators (i.e. one of the UI objects 2) at the time in accordance with a scientifically proven eye contact pattern e.g. while practicing the speech. For example, the user 1 may be instructed to look at a highlighted (e.g. by a solid border) UI object 2'. After a while, another UI object 2' may be highlighted as illustrated by the arrows in FIGS. 2*b* and 2*c*. Then the user should move his/her gaze to the new highlighted UI object 2' (the apostrophe in the reference indicates that the particular UI object corresponds to a "desired" gaze area 3). In this way, the user may be trained in order to maintain a certain behaviour, when giving the real speech. The user 1 should then of course focus of the real spectators instead of the UI objects 2, but the behaviour would be the same. This will typically improve the spectators listening experience.

For example, the user 1 is first instructed to look at the spectator to the left for a certain time period, as illustrated in FIG. 2*a*, where the left-most spectator is presented by a solid line, while the other spectators are presented with dashed lines. After a certain time, the user is instructed to instead look at the spectator in the middle, as illustrated in FIG. 2*b*, where the spectator in the middle is instead presented by a solid line. Finally, the user is instructed to look at the spectator to the right, as indicated in FIG. 2*c*. The user's actual gaze may at the same time be traced to check if the user follows the instructions. This is done by comparing the users actual gaze with the gaze area 3 corresponding to the UI object 2, at which the user is instructed to look. The gaze area (or areas) at which the user 1 is instructed to look is herein referred to as a desired gaze area. Hence, some of the UI objects 2 (here indicated by dashed lines) may represent gaze areas 3 which are not desired right now.

Figure 3A:
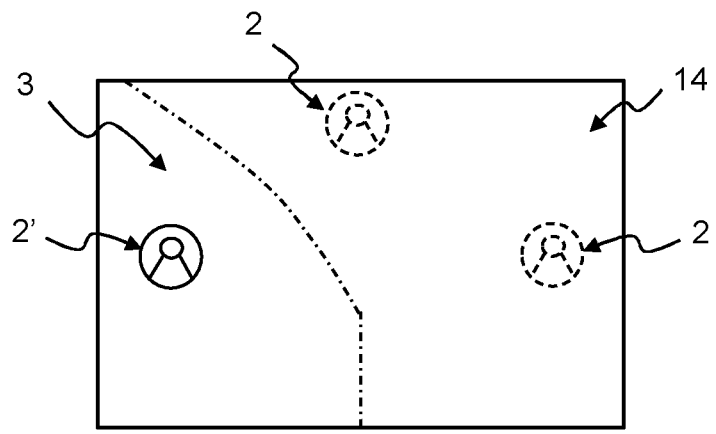
FIGS. 3a to 3c illustrate a display comprising UI objects representing different desired gaze areas according to one example embodiment.
Figure 3B:
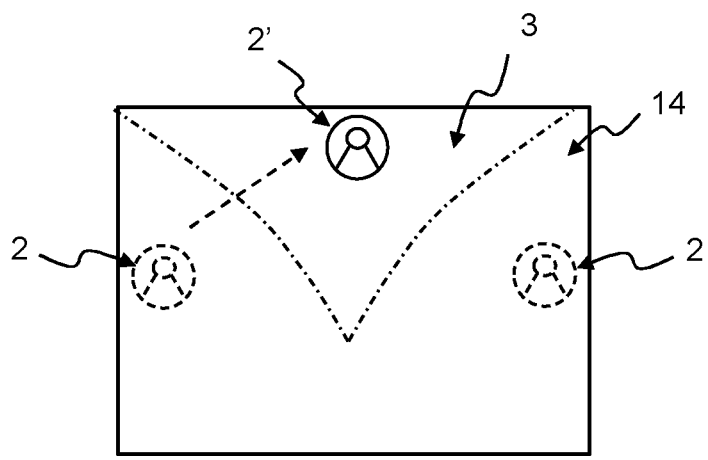
Figure 3C:
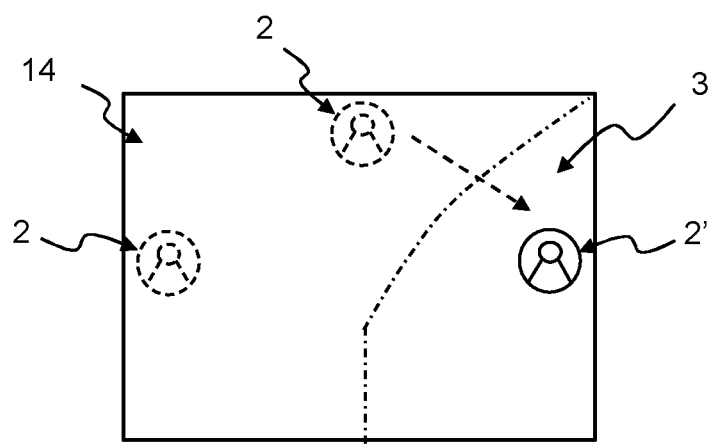

FIGS. 3*a* to 3*c* illustrate a display comprising the same UI objects 2 according to another example embodiment, where the gaze areas 3 (indicated by dash-dotted borders) are not overlapping. In FIGS. 3*a* to 3*c* the desired gaze area 3 is moved from the left to the right in the same way as in FIGS. 2*a* to 2*c*.

The proposed technique will now be described in further detail with reference to the flowchart of FIG. 4, which illustrates the proposed method for conducting a user's gaze direction according to one embodiment. The method may be performed at any time, typically during normal operation of an electronic user device 11. The method is typically implemented in a control device 11 of the electronic user device 1 (FIG. 5).

The steps of the method may be defined in a computer program, comprising instructions which, when the program is executed by processors (e.g. control device 11), causes the electronic user device 10 to carry out the method. The steps of the method may also be defined in a computer-readable medium, e.g. an internal memory 15 of the electronic user device 10 and/or in any other memory. The computer-readable medium comprises instructions that, when executed by a control device 11, causes the electronic user device 10 to carry out the method. The procedure may be initiated by a user starting a certain software application on the electronic user device 10. For the speech training example, the user may for example start a speech training program.

Then the software application is started, and initial UI is typically displayed. The initial UI may for example provide instructions to the user. The user may also be asked to input information. For example, the user may be asked to select between different training modes, such a one-to-one or virtual audience training. The user may also select difficulty and speed of the training. The user may also be requested for a program or file to run in the background. The software application may also initiate different functionality in the electronic user device 10, such as a camera 13 and a display 14 (FIG. 5). For example, speech recording may be started, if the method performs the conducting based on the user's speech. In other words, in some embodiments, the method comprises recording S0 a speech signal representing the user's speech. The recording typically continues while performing the succeeding steps.

Then the user interface for guiding the user's gaze is presented. In other words, the method comprises presenting S1, on the one or more displays 14, one or more UI objects 2 indicative of one or more desired gaze areas 3. In other words, a UI object that guides the user to look in a certain direction is presented on the one or more displays 14. For example, one or more avatars representing a virtual audience are displayed on top of, i.e. overlaid on a background image, as illustrated in FIGS. 2 and 3. The background image is for example speech notes, such as PowerPoint slides, of the user. The number of UI objects 2 are for example three as in FIGS. 2 and 3, but it may also be fewer or less depending on the application and the size of the one or more displays. In other words, in some embodiments, the one or more UI objects 2 comprises a plurality UI objects positioned on distinct parts of the one or more displays 14 and representing individual gaze areas 3.

In some embodiments, the background image comprises speech information related to a speech to be performed by the user. The speech information may e.g. be speaker notes or information to be displayed to an audience, e.g. power point slides. The background image may also be a meeting software. The meeting software may then include speech information, such as a presentation. In other words, in some embodiments the presenting S1 comprises presenting speech information related to a speech to be performed by the user. The speech information is typically dynamic and may change automatically over time or via a trigger e.g. when a user changes slide in the presentation.

The one or more UI objects 2 in some embodiments, comprises a plurality UI objects 2 positioned on distinct parts of the one or more displays 14 and representing individual gaze areas 3. The gaze areas 3 may be separate (FIG. 3) or overlapping (FIG. 2). Alternatively, fewer UI objects 2 are used. For example, one or more UI objects shaped as arrows may instruct the user 1 where to look. The one or more UI objects 2 may even instruct the user to look outside the one or more displays 14, for example by letting a UI object shaped as an arrow point at a gaze area 3 outside the one or more displays 14. For example, at a person behind the electronic user device 2 or to another object next to the electronic user device 2 or to another component of the electronic user device 2. In other words, in some embodiments, the one or more desired gaze areas 3 are positioned on the one or more displays 14 or outside the one or more displays 14.

In some embodiments, the one or more UI objects 2 comprises one single UI object positioned on the one or more displays. For example, one UI object 2 is positioned centrally or right below the camera in order to direct the user's gaze into the camera as illustrated in FIG. 1, which may e.g. be desirable in a conference call or similar.

If there is a plurality of UI objects 2, then they may be positioned in different ways. For example, one UI object may be presented in each corner of the display 14. The UI objects 2 may either be displayed simultaneously or one at the time. The UI objects 2 may have any suitable design. For example, it may be a pair of eyes, a face, a sign, a geometric shape, a text field etc. If the UI objects 2 are avatars, then they may represent different people (e.g., women, men, European, Asian, etc.).

If there are multiple UI objects 2, then the user may be instructed to look at one (or a subset) of them. In other words, in some embodiments, the method comprises continually indicating S2 to the user 10 one UI object 2' of a plurality of UI objects 2, 2' which represents a desired gaze area 3. The UI objects 2 may be highlighted in different ways e.g. by different borders, colours or blinking, such that the user 1 may easily understand at which UI object 2 to look.

If the UI objects 2 represents spectators, then one of the spectators, with whom eye contact should be established may be indicated. The one spectator may be selected in accordance with a gaze movement pattern corresponding to "good" eye contact as will be further described below. In other words, in some embodiments, the continually indicating S2 comprises indicating one spectator of the one or more of the spectators, with whom eye contact should be established.

The conducting of the user's gaze is then initiated for example, when the user 1 presses a button "Enter". A countdown may then start while opening the camera and the user getting ready. The gaze tracking then starts.

The method then comprises obtaining S3, using the camera 13, eye-gaze data indicative of the user's actual gaze direction d. This may be done using known techniques, such as disclosed in US2018081434 A1. Typically, both eyes are traced, but in certain scenarios it may be enough to trace one eye, such as if one eye is hidden because of an angle or a shadow. Also, for better accuracy or quality several cameras 13 may of course be used, if available.

Typically, face and eye recognition are performed for determining gaze tracking. First the face region is detected using for example Open Source functions such as OpenCV. Then, within the face region, a neural network may be used to track face feature points. Finally, the position of the pupils may be detected. In some embodiments, an amount of eyes white on respective side of the pupils is determined to determine the position of the pupils within the eyes. Eye tracking could be improved by estimating the pose of the user. Hence, in some embodiments, the user may be instructed e.g. by a text string to change pose. In other words, in some embodiments, the obtaining S3 comprises estimating at least one of pupil centre, eye fixation time, eye glint data, pupil dilation and constriction, blink rates, and corneal reflection.

The user's actual gaze direction is then compared to the gaze direction revealed from the eye gaze data. Stated differently, the method further comprises evaluating S4 the user's gaze direction by analysing an extent to which the user's actual gaze direction indicated by the eye-gaze data corresponds to the one or more desired gaze areas 3. That the gaze direction indicated by the eye-gaze data corresponds to the one or more desired gaze areas 3 herein refers to that the user gaze is directed within the desired gaze area. This is typically done by estimating a gaze position, i.e. the position e.g. at one of the one or more displays 14, where the user looks, based on the gaze data and checking whether the gaze position is within the desired gaze area 3. If the user's physical position is known (or estimated or anticipated) and the gaze direction is estimated, then the gaze position may be estimated. One way of estimating the gaze direction is to find centre of the eyes and the position of the pupil. From this information a gaze direction can be geometrically calculated. It is then possible to geometrically calculate where the user is looking. The user's position may be anticipated as a fixed distance from the camera. Alternatively, it may be estimated based on image data captured by the camera 13.

If the UI objects represent a virtual audience, then the evaluating S4 comprises analysing a level of eye contact between the user 10 and the virtual audience using one or more rules defining a level of eye contact. For example, if one spectator has been indicated (as being the one to establish eye contact with), then the evaluating S4 comprises evaluating a level of eye contact between the user 10 and the indicated spectator. As previously stated, any rules defining "good" eye contact may be used. There is various scientific research regarding how a speaker should gaze for the listeners to perceive eye contact. In some embodiments, the one or more rules comprises a minimum and/or maximum time the user's gaze direction should constantly remain on a gaze area 3 represented by one of the spectators. In some embodiments, minimum time corresponds to an estimated time it takes for the user to say at least one sentence. A time interval between two spectators may be calculated as follows. If the speed of the speech in minutes (Speed_min) is 135 words/min, then the speed in seconds is defined as:

$$\text{Speed}_s = \frac{\text{Speed}_{min}}{60} = 135/60 = 2.25 \text{ words/s}$$

Then, the time to say a word is defined as:

Time_word=1/Speed_s=1/2.25=0.4444 s

Then, if one pause at least every 17 words is desired, the UI object shall move at least every:

$$\text{Time}_{interval} = \left(\frac{1}{\text{Pause}_{frequency}}\right) * \text{Time}_{word} = (17 * 0.4444) = (17 * 60)/135 = 7.55 \text{ s}$$

If a speech signal is also recorded, then the speech signal may also be used to evaluate the level of eye contact. For example, it may be desirable to move the gaze between the UI objects 2 between the words, instead of while actually speaking. Hence, silent periods in the speech signal may be detected and eye contact may be considered to be "good" if the user 1 only moves his/her gaze during these silent periods. In other words, in some embodiments, the evaluating S4 is also based on a speech pattern of the recorded speech signal. Thus, the evaluation S4 may evaluate any criteria depending on the implementation.

Another possibility is to use text analysis of e.g. speech notes or speech information in order to determine suitable moments to move the gaze from one spectator to the other or to determine parts of the speech where high level of eye-contact is required. In other words, in some embodiments the rules are based on speech information. The speech information may correspond to speech information presented on the display. Alternatively, the user may enter a specific text file comprising the speech, which is compared to the recorded speech signal.

The rules may define certain parts (in time) of the speech where good eye contact is important. The certain part may be where essential information is presented, so that the attention of the audience is crucial. Such portions may be identified using certain phrases in the speech information. Alternatively, tags may be included in the speech information to identify these parts. In other words, in some embodiments the rules are based on phrases or tags in the speech information. The rules may then be configured such that an amount of eye-contact that is required for "correct gaze direction" varies over the speech. In other words, the requirement for "good" eye contact may be higher at certain parts of a speech. In this way the user can be trained to pay attention to having extra good eye-contact during these parts of the speech. This may for example be implemented by changing the user interface object 2 indicative if the desired gaze area 3. For example, the colour or pattern of the user interface object 2 may be changed to remind the user about the eye-contact.

Important parts of the speech may also be defined by one or more timings within a speech performed by a user. The timings may be defined by certain time period, time stamps or similar. For example, the beginning and/or the end of the speech may be more important (e.g. the first or last 10 minutes). Alternatively, a part where e.g. a sales pitch is presented may be considered most important. It may also be important with good eye-contact when clearing or clarifying a certain slide of a presentation to the audience. For example, a part of a speech where predefined object types such as charts, timelines or complex pictures are presented may be considered as an important part of the speech. In other words, in some embodiments the rules are based on a timing (e.g. a certain point in time) within a speech to be performed by a user. Alternatively, important parts of the speech may be detected by detecting the predefined object types by software using for example object recognition. The important parts may then be automatically detected without any timing information.

If only one spectator is presented on the display, which may be the case when practicing an online presentation, the rule may define a minimum part of the time (e.g. 50%) that the user should look into the camera. The desired gaze area 3 (here the camera 13) is then for example represented by a virtual spectator or other user interface object 2 presented in vicinity of the camera. As described above this percentage may vary over time. In some embodiments, the rules are based on the importance of the slides. In some embodiments, the speech information comprises digital (e.g. software) tags or markers indicative of important parts of the speech. These tags or markers may be recognised by the software and considered by the rules for evaluating eye-contact, when for example a tagged slide is presented on the display. The rules may for example change a level of eye-contact (e.g. a percentage of threshold) required for "good" eye-contact based on the importance of the slides. The tags and markers may also be used to remind the user 1 about the eye contact at important slides, for example by changing the user interface object 2 indicative of the desired gaze area 3.

The user is then given information regarding whether the gaze direction is correct. This is typically done continually, substantially in real-time. The feedback may for example be a visible indicator or a tactile signal transmitted via a wearable device such as a smart watch. In other words, the method further comprises providing S5 user feedback indicative of a result of the evaluation S4 to the user. In some embodiments, the user-feedback comprises a visible, an audible or a tactile signal.

In some embodiments, some delay is added to the user feedback. This may be relevant when the user feedback is negative, as it might be an occasional deviation e.g. due to someone entering the room or similar. However, feedback about correct, i.e. desirable, gaze direction may typically be given without delay. Alternatively, negative feedback may be associated with some kind of time window or threshold. Hence, negative feedback may not be provided until the gaze direction has indicated a deviation from the desired gaze area 3 for a certain amount of time.

Figure 6A:
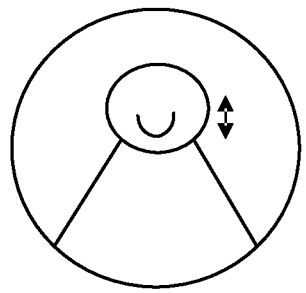
FIGS. 6a and 6b illustrate some examples of visible user feedback.
Figure 6B:
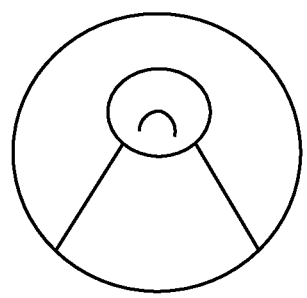

FIGS. 6a and 6b illustrate some examples of visible user feedback. In one example implementation a UI object 2 being an avatar smiles and nods once eye contact is detected, as illustrated in FIG. 6a. When eye contact is lost the avatar immediately rises his eyebrows and has a sad face, as illustrated in FIG. 6b (left avatar). After a predefined amount of time without eye contact, e.g. of about 1 sec, the avatar starts waving at the user asking for attention and eye contact (right avatar).

Additional feedback may be given to the user 1 during eye contact training. For example, if it is detected that the user 1 has constantly looked at the current UI object 2 while constantly speaking without making any long pauses (i.e., pauses longer than 1 sec) during a time falling in the interval [(Time$_{interval}$)−2 sec, Time$_{interval}$] and only then has made a long pause (i.e., a 1-2 sec pause), a "Good job!" sign (for example "thumbs-up") appears somewhere on the one or more displays (e.g., in-between the current UI object and the next UI object, next to the current UI object, etc.). Any other behaviour than the one described above may be considered wrong. For example, if the user while speaking looks away from the indicated UI object 2. Then, the user needs to be warned (e.g., a stop hand sign may appear in place of the current UI object or a focus sign may appear in place of the current UI object 2 or the current UI object 2 may flash.

Since the average reaction time to a visual stimulus for humans is 0.25 sec, the detection time (i.e., the time the software shall use to realize whether the user has looked at the current UI object 2 or not) may be 0.25 sec. Then, a reaction, if required, should take place (e.g. the "stop" sign shall appear in place of the current UI object 2).

The number of positive detections (i.e. "Good job!" signs such as an exclamation mark) appearing during a certain time (e.g. one slide or a complete presentation) may be counted. The feedback to the user 1 may be provided in terms of numbers of positive detections. For example, if the user has made at least 70% of positive detections, user feedback in a post-presentation report may be "Good eye contact" and if less "Poor eye contact".

The desired gaze area 3 might change over time. For example, the UI objects 2 and corresponding gaze areas 3 may be moved around on the one or more displays. Alternatively, if there is a plurality of UI objects 2 then another UI objects 2 may be highlighted, which means that a new desired gaze area 3 is selected. Accordingly, the method also needs to be repeated. In other words, in some embodiments, the method comprises continually repeating the presenting S1, the obtaining S3 and the evaluating S4 and providing S5 the user-feedback indicative of the result of the evaluating S4 to the user continually or at least substantially in real time.

In some embodiments, the method comprises, moving S6 the desired gaze area in response to one or more triggers. In some embodiments, the one or more triggers comprises one or more of; a user input, expiry of a timer, detection of particular words or phrases and detection of a silent period in a recorded speech signal.

In some embodiments, the user is instructed to look at the UI objects 2 in an anti-clockwise fashion, starting from the bottom left UI object 2 and ending to the top left UI object 2. Furthermore, the user 1 needs to know to which UI object 2 to look at, at any certain time. For example, the current UI object 2 may be highlighted (e.g., in green, in bold, etc.) to indicate to the user that in that moment he/she has to look at that specific UI object 2 out of the plurality of UI object 2.

During speech training, if a maximum time (Time$_{interval}$) the user 1 should look at a certain UI object 2 is defined as described above, then the user 1 needs to be warned when the time to look at the current UI object 2 is running out, so that he/she may be able to finish a sentence. Thus, during the last seconds (e.g., 2 sec) the UI object may flash three times, turn red, fade out, etc. The next UI object may be highlighted (or appear) at a time equal to (Time$_{interval}$+pause) or when a long pause is detected.

An example implementation of moving the desired gaze area 3 during eye contact training using the proposed technique will now be briefly described.
1) After about 5 sec from starting eye contact the frame around a UI object 2 (e.g. an avatar) indicating a present desired gaze area 3 starts blinking, which indicates to the user 1 that it is time to move to a new avatar and to establish new eye contact. The user 1 is about to pass the 7.55 sec time limit. The user 1 should then take a pause before changing avatar.
2) When the user is ready, he presses the space bar to change desired gaze area 3/UI object 2 (the switch can be done when silent period of more than 1 sec is detected. Alternatively, the change desired gaze area 3/UI object 2 is switched automatically based on a time interval or based on detection on key words such change now or similar.
3) After pressing the space bar, the timer is re-set for counting the 7.55 sec. Before 5 seconds has passed, the space bar is disactivated. After 5 seconds the new UI object starts blinking and step 1 is repeated.
4) When changing the slide, the gaze area 3 is back to the initial UI object 2 on the left.

This is one example of how the desired gaze area 3 may be moved in accordance with a recognised pattern for "good" eye contact. However, other patterns may also be used. Also, the way the desired gaze area 3 is moved may be implemented in other ways. For example, automatically or based on suitable pauses in a recorded speech signal. In other words, in some embodiments, the moving S6 comprises moving the desired gaze area between the one or more gaze areas 3, according to a pre-defined eye contact training pattern.

Figure 9A:
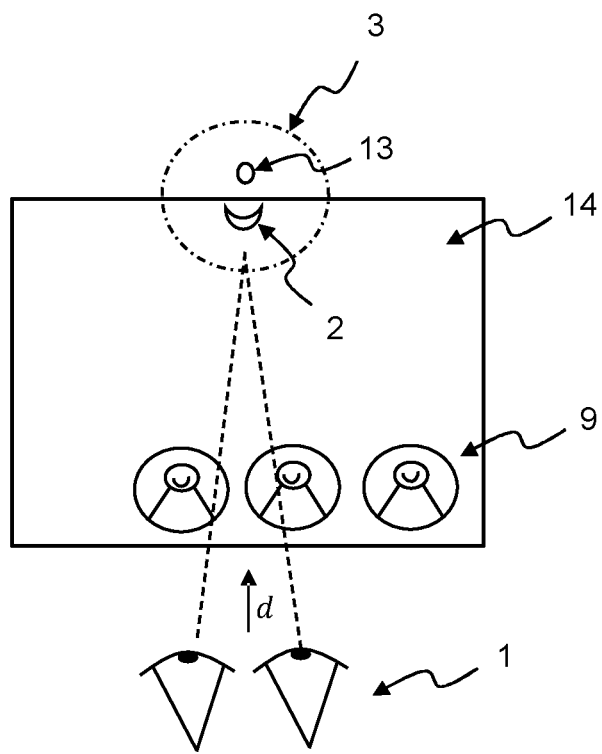
FIGS. 9a and 9b illustrate embodiments of training eye-contact in an on-line speech scenario.
Figure 9B:
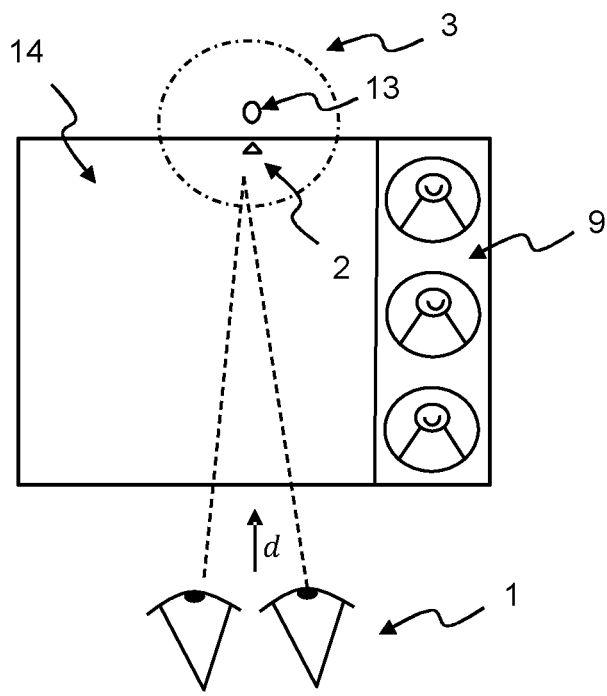

FIGS. 9A and 9B illustrate embodiments of training eye-contact in an on-line speech scenario. In this example, the background image corresponds to a virtual meeting software, such as Zoom, Microsoft Teams or Google Meet. In such software images of the other participants (i.e. the spectators) may be placed differently on the displayed compared to the examples above. For example, the audience 9 may be placed at the bottom left (FIG. 9A), to the right (FIG. 9B) or under the camera. However, a desired gaze area 3 for "good" eye-contact is an area at or around the camera 13. Hence, the images of the audience 9 at the display 14 may differ from a desired gaze area 3 corresponding to "good" perceived eye-contact. Therefore, in these embodiments another symbol or object is used to indicate the desired gaze area 3. For example, the user interface object 2 may be a separate user interface object that teaches or reminds the user 1 where to look. In the illustrated example a user interface object 2 shaped like a "moon" is presented S1 on the display 14 right below the camera 13. The user interface object 2 indicates the desired gaze area 3 which corresponds to good perceived eye-contact with on-line spectators 9. In other words, the user interface object 2 represents an audience placed on the "other side" of the camera.

In these embodiments eye-gaze data is then obtained S3 in the same way as described above. The user's gaze direction is then evaluated S4 based on one or more rules defining a level of eye contact by analysing an extent to which the user's actual gaze direction indicated by the eye-gaze data corresponds to the one or more desired gaze areas 3. In other words, the evaluating S4 comprises evaluating to which extent the user 1 looks into the camera. The evaluating S4 may be performed in different ways, e.g. depending on how well the user's gaze may be traced. For example, eye-contact is considered good or acceptable when the user looks into the camera at least ⅗ of the time. The criteria may also define a minimum time that the user shall look into the camera before looking away e.g. 3 seconds or a maximum time that the user 1 is allowed to look away.

If a speech signal is recorded S0, then eye contact may be evaluated based on the speech signal. For example, eye contact is only required when the user 1 is speaking. This may be particularly relevant in a meeting where several participants are speaking alternately.

User feedback indicative of a result of the evaluation to the user may be provided S5 during and/or after the training. During the training gentle feedback is typically provided in order not to distract the user 1 too much. For example, the user interface object 2 changes colour, texture or similar to encourage the user to look into the camera. This may be done when eye contact is bad and/or at important parts of speech, as described above.

After the training, a summary of the training may be displayed. For example, user feedback may be given about an overall level of perceived eye-contact. The user feedback may also indicate performance during certain parts of the speech. For example, the user may be informed that eye-contact was not sufficient at an important part of the speech or at the end of the speech.

The training according to these embodiments be performed either "live" or via a training software. Hence, the method may either be implemented as a training program, where the audience are some kind of avatars. However, the training may also take place in a live meeting, such that the user is trained during a real performance.

In some alternative embodiments the step of presenting S1 one or more user interface objects indicative of one or more desired gaze areas on the display may be omitted. This could for example be in a more advanced mode of the training, where the user is supposed to have adapted the desirable behaviour. In this case the desired gaze areas 3 are instead configured S1' (e.g. stored) in the control device 11 and the user 1 is assumed to know where to look (i.e. being aware of the desired gaze area). For example, the user 1 knows that he or she is expected to look into the camera 13 and is provided user feedback indicating if the actual gaze direction corresponds to good eye-contact or not. The user feedback may in these embodiments be provided in real time or after the performance. In some embodiments the user interface object 2 is triggered to be displayed in certain situations, such as at important parts of the speech or if eye-contact is below a threshold. For example, if a user 1 runs the proposed technique when participating in a conference call, then the one or more user interface objects 2 are displayed upon the user's gaze direction corresponding to the desired gaze area for less than a certain amount (e.g. ½, ⅖ or ⅗) of the time. The time is in some embodiments the total time or alternatively only the time when the user is speaking, which is known from a recorded speech signal as discussed above.

Figure 4:
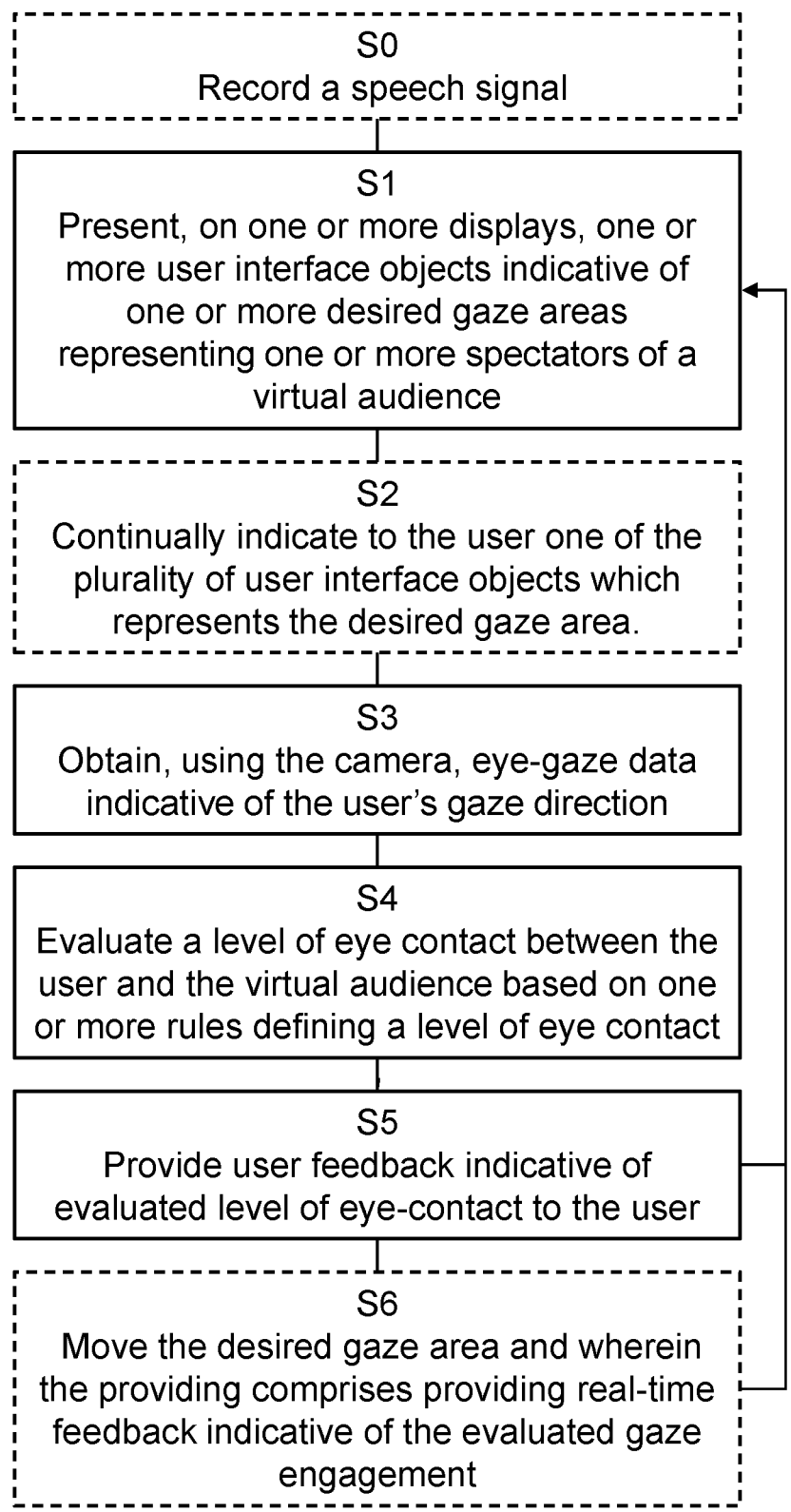
FIG. 4 illustrates the proposed method for conducting a user's gaze direction.
Figure 5:
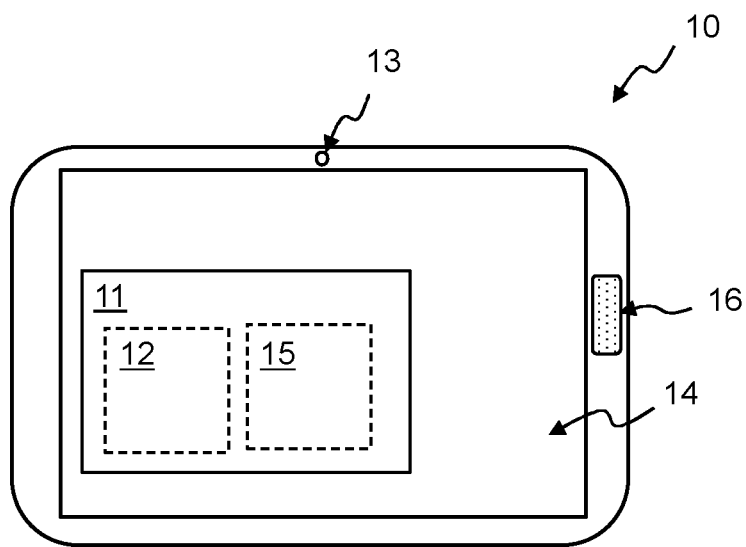
FIG. 5 illustrates an electronic user device according to one example embodiment.

The disclosure also relates to a corresponding electronic user device 10 (FIG. 5) configured to execute the method of FIG. 4. The electronic user device 10 is typically a personal computer (laptop or stationary computer), but it might as well be a tablet or similar or any electronic device. The electronic user device 10 comprises a control device 11, a camera 13 and a display 14. The electronic user device 10 typically also comprises other electronics not shown in FIG. 5, such as a communication interface and input device, for example physical buttons, or touch buttons.

The display 14 may be a built-in display, such as a display 14 of a laptop or tablet. In some embodiments the display 14 is an external or separate display connected to the control device 11 wirelessly or by wire. In the same way the camera 13 may either be an integrated camera or an external camera device. In some embodiments, the electronic user device 10 comprises more than one display 14 and/or more than one camera 13. For example, the electronic user device 10 may be a computer (stationary or laptop) connected to two (or more) external displays 14. Hence, in some embodiments, the electronic user device 10 is a unit in a functional sense as it may comprise several physically devices connected wirelessly or by wire. For example, in some embodiments the electronic user device 10 is a personal computer and one or more connected devices e.g. external displays 14 and/or cameras 13.

The control device 11 comprises at least one processor 12 and memory 15. In general, the electronic user device 10, or more specifically the control device 11 is configured to perform all embodiments of the method described herein. This might e.g. be achieved by executing software stored in the memory 15 that causes the control device 11 to perform the method. More specifically, the control device 11 is configured to present, on the one or more displays 14, one or more UI objects 2 indicative of one or more desired gaze areas 3 and to obtain, using the camera 13, eye-gaze data indicative of the user's actual gaze direction. The control device 10 is also configured to evaluate the user's gaze direction by analysing an extent to which the user's actual gaze direction indicated by the eye-gaze data corresponds to the one or more desired gaze areas 3 and to provide user feedback indicative of a result of the evaluation to the user.

According to some embodiments the one or more UI objects 2 comprises one single UI object positioned on the one or more displays.

According to some embodiments the one or more UI objects 2 comprises a plurality UI objects positioned on distinct parts of the one or more displays 14 and representing individual gaze areas 3.

According to some embodiments the control device 10 is configured to continually indicate to a user 1 one UI object 2' of the plurality of UI objects 2, 2' which represents a desired gaze area 3.

According to some embodiments the control device 10 is configured to continually present the one or more UI objects 2, obtaining gaze data, evaluate the user's gaze direction and to provide user-feedback indicative of the result of the evaluation to the user in real-time.

According to some embodiments the control device 10 is configured to move the desired gaze area in response to one or more triggers.

According to some embodiments the one or more triggers comprises one or more of a user input, expiry of a timer, and detection of a silent period in a recorded speech signal.

According to some embodiments, the control device 10 is configured to obtain the gaze direction by estimating at least one of pupil centre, eye fixation time, eye glint data, pupil dilation and constriction, blink rates, and corneal reflection.

According to some embodiments, the one or more desired gaze areas 3 are positioned on the one or more displays 14 or outside the one or more displays 14.

According to some embodiments, the user-feedback comprises a visible, an audible or a tactile signal.

According to some embodiments, the presented UI objects 2 represent one or more spectators of a virtual audience of the user 10 and the control device is configured to analyse a level of eye contact between the user 10 and the virtual audience using one or more rules defining a level of eye contact.

According to some embodiments, the one or more rules comprises a minimum and/or maximum time the user's gaze direction should constantly remain on a gaze area 3 represented by one of the spectators.

According to some embodiments, the minimum time corresponds to an estimated time it takes for the user to say at least one sentence.

According to some embodiments, the control device 10 is configured to moving the desired gaze area between the one or more gaze areas 3, according to a pre-defined eye contact training pattern.

According to some embodiments, the control device 10 is configured to continually indicate one spectator of the one or more of the spectators, with whom eye contact should be established and evaluate a level of eye contact between the user 10 and the indicated spectator.

According to some embodiments, the control device 10 is configured to record a speech signal representing the user's speech and to evaluate the user's gaze direction based on a speech pattern of the recorded speech signal.

Figure 7A:
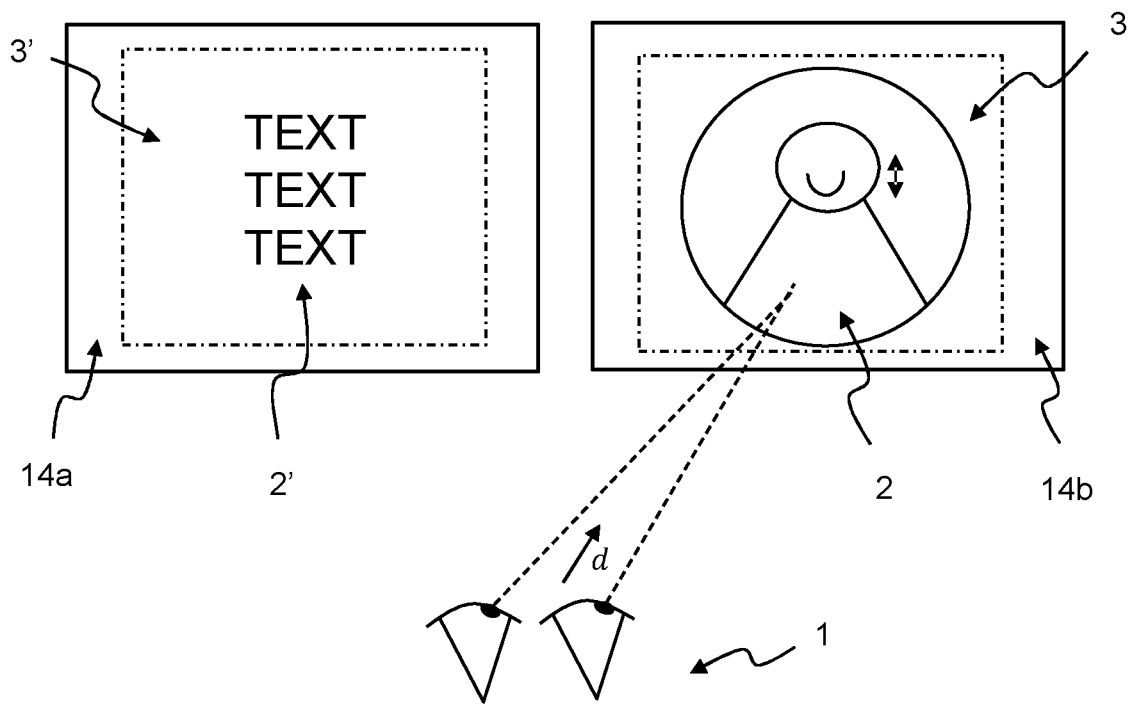
FIGS. 7a and 7b one example embodiment of the proposed user interface.
Figure 7B:
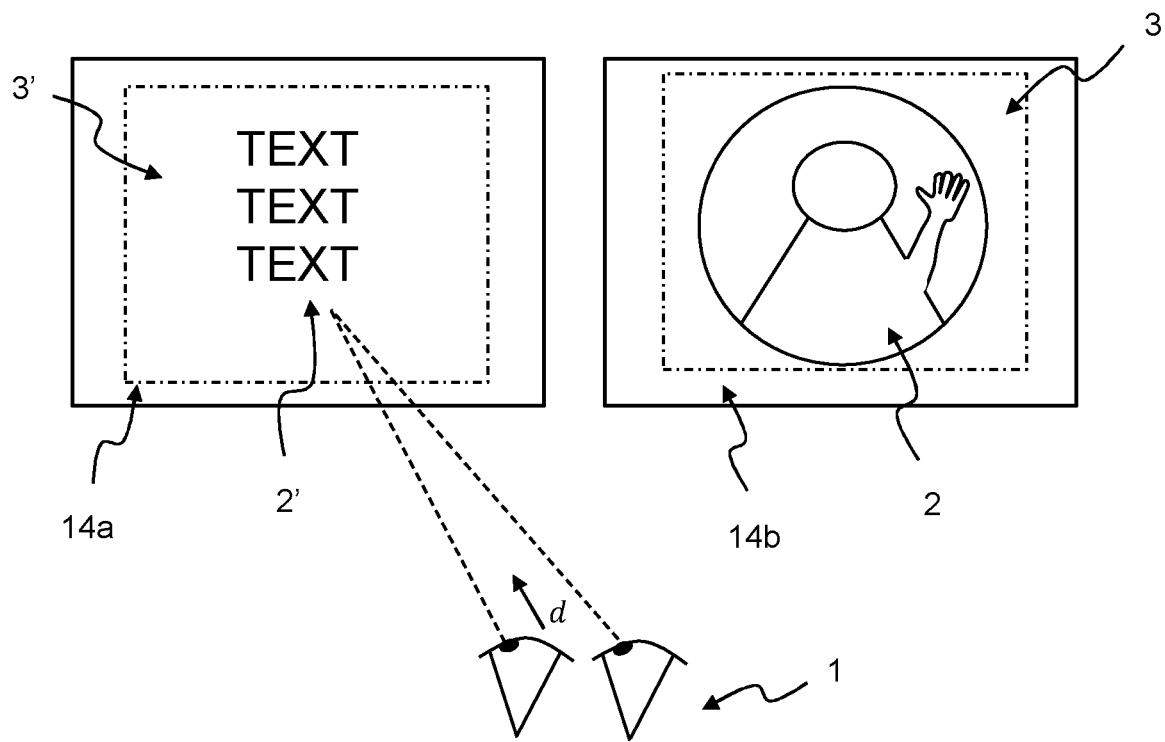

FIGS. 7a and 7b one example scenario, where the proposed technique may be implemented. This example scenario relates to speech training exercise where a user 1 may practice giving a presentation e.g. to one spectator.

In this embodiment the electronic user device 10 comprises two displays 14 (denoted 14a and 14b). A user interface object 2, illustrated as an avatar representing the spectator, defines a desired gaze area 3 on the right display 14b. On the left display 14a, the users speaking notes e.g. a ppt presentation is displayed. In this scenario, it is typically desirable that the user 1 looks at the spectator on display 14b (i.e. at the desired gaze area 3) while speaking. However, the user 1 should typically also look at the text on the left display 14a now and then.

As stated above, the evaluating S4 (described n connection to FIG. 4) may comprise evaluating a set of rules. The rules may for example be that the user's gaze direction d is directed at the desired gaze area 3 while speaking (at least to a certain amount), as illustrated in FIG. 7a. However, the user 1 may look away (e.g. at the text) now and then to for example check the speaking notes on the left display 14a, as illustrated in FIG. 7b.

User feedback may be continuously be provided S5 to the user 1 in different ways. In the illustrated example, the avatar nods when the user's gaze direction d is directed at the desired gaze area 3, in order to confirm "good" eye contact. On the other hand, if the user 1 fails to look at the avatar while speaking, the user's attention is called for, e.g. by the avatar waving (FIG. 7b). The waving is typically triggered when the user 1 has spoken for a predetermined time (e.g. 4 seconds), without looking at the avatar.

Alternatively, the set of rules may state that the user's gaze direction d should be directed at the desired gaze area more than 70% of the time. In some embodiments, the text is also a user interface object 2' defining a gaze area 3' on the left display 14a. Then the set of rules may comprise that the user should also look at the desired gaze area 3' represented by the text now and then. This would typically make the presentation better and assure that the user 1 follows his script.

In some embodiments, an object (e.g. a garment or a user interface) is presented on the left display 14*a*, instead of the text. This may be the case when a user should practice describing an object to a spectator, for example in a sales scenario. Then an image of an object being a product to sell may be presented on the left display 14*a*.

Figure 8A:
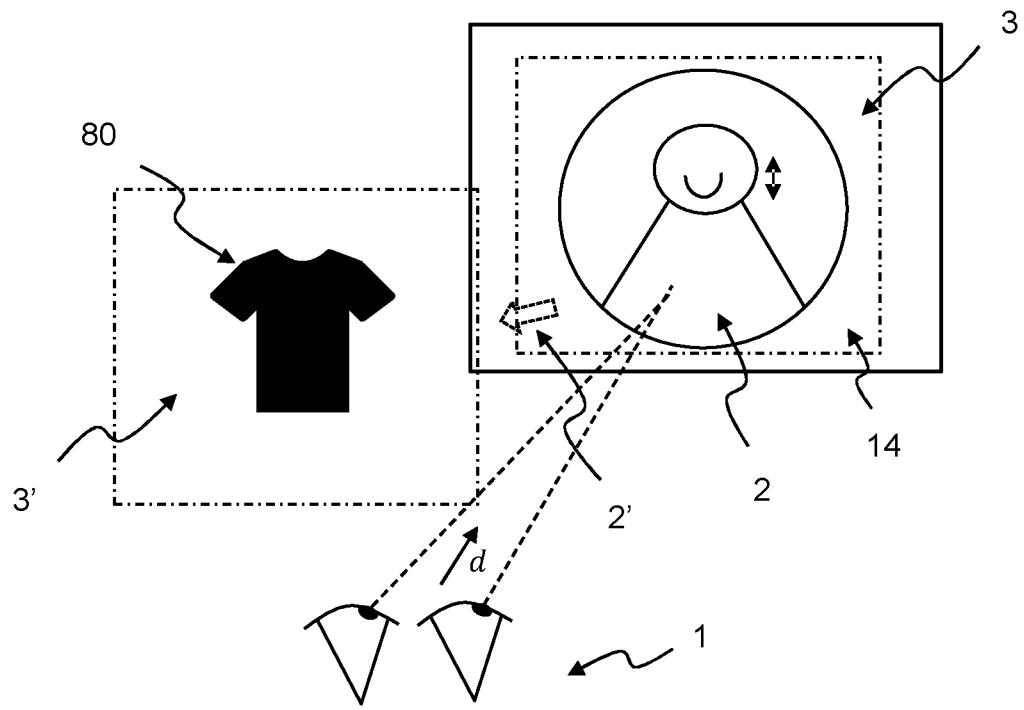
FIGS. 8a and 8b another example embodiment of the proposed user interface.
Figure 8B:
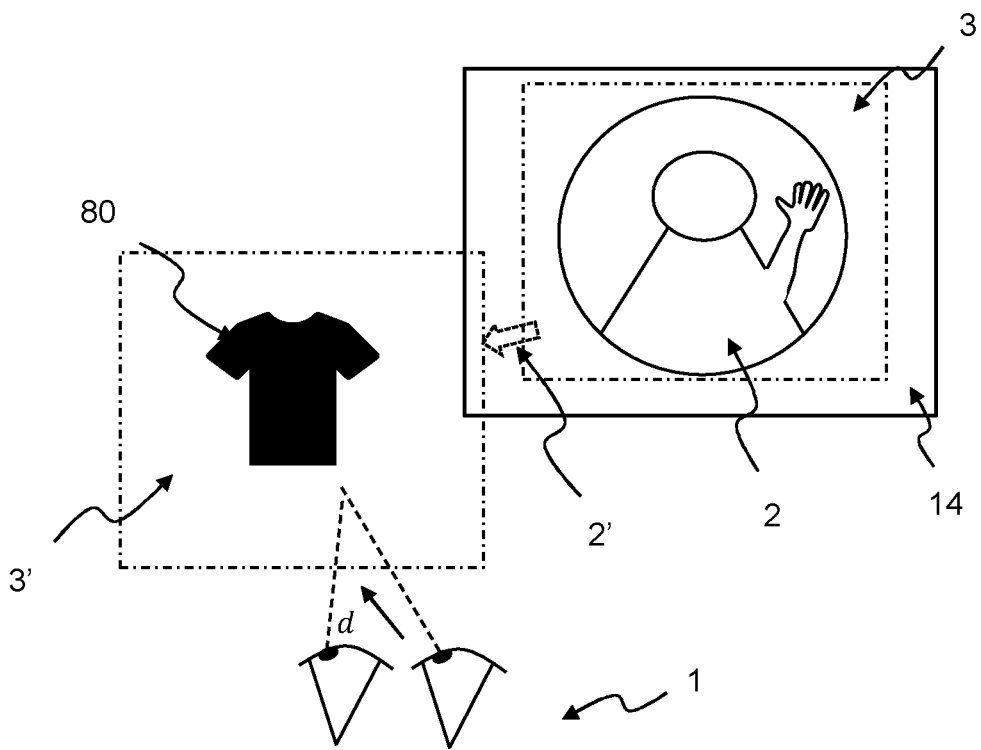

FIGS. 8*a* and 8*b* one example scenario, where the proposed technique may be implemented. This example scenario relates to speech training exercise where a user may practice describing a real object 80 (i.e. in the real-world) to a user 1.

In this example embodiment the electronic user device 10 comprises one display 14. A user interface object 2, illustrated as an avatar representing the spectator, defines a desired gaze area 3 on the display 14. In this scenario, the user 1 shall try to establish eye contact with the spectator represented by the avatar, while describing the object. In this scenario, the user should typically look at the spectator while speaking (FIG. 8*a*) and during silent periods the user should look at the object 80 (FIG. 8*b*), to also draw attention at the object 80. In some embodiments, another desired gaze area 3' is used to verify that the user 1 also looks at the "real-world" object 80. This desired gaze area 3' may be represented by a corresponding user interface object 2', illustrated as an arrow pointing at the object outside the display 14, presented on the display 14.

A desired gaze pattern is then be defined by the set of rules used in the evaluating S4 step and user feedback is provided S5 to the user accordingly. For example, the avatar nods (FIG. 8*a*) to indicate "good" eye contact (gaze direction d is directed at the desired gaze area 3) and waves when eye contact is lost (FIG. 8*b*). Also, the arrow may be highlighted (e.g. by colour or flashing) when the user 1 forgets to look at the object now and then.

Above, the proposed technique has been presented in the context of eye-contact training. However, it must be appreciated that the proposed method for conducting a user's gaze may be used also in other applications.

In a second example, the technique may be used while driving a vehicle, such as car or motorbike. The desired gaze areas 3 may then represent regions of interest, such as certain signs or objects close to the vehicle. If detected that the user 1 is not looking at specific gaze areas 3, it could display on the windshield (or dashboard) or helmet's visor a UI object pointing in the right detection. Alternatively, an audible or tactile signal may be provided. The regions to look at can determined by a combination of an external camera, a radar and GPS. There are also some rules to follow such you should look first left and then right while turning on a crossroad (in this part of the world). The proposed technique may be implemented in a tool for learning to drive or after as driving assistant.

The technique may also be implemented in gaming applications. The proposed technique may help players to identify objects in the game in case they are not looking at them (e.g. thesaurus or enemies). This can be done to aid the player while playing or for training purposes. Imagine you have several enemies coming against you, the proposed technique may be used to help the user to look in a particular area to maximize the killing ratio both during live and training sessions.

While playing a car game, we could point left or right to help a user cover the angle while another drive is taking over.

The proposed technique may also be used to make a user look at banners on website. For example, if the user is not looking at the banners, they may start flashing to draw attention to them.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A computer-implemented method for eye-contact training comprising:
   at an electronic user device comprising one or more displays and a camera:
   recording a speech signal representing a user's speech,
   presenting, on the one or more displays, one or more user interface objects indicative of one or more desired gaze areas representing one or more spectators of a virtual audience of the user,
   obtaining, using the camera, eye-gaze data indicative of the user's actual gaze direction,
   evaluating a level of eye contact between the user and the virtual audience based on one or more rules defining a level of eye contact, by analysing an extent to which the user's actual gaze direction indicated by the eye-gaze data corresponds to the one or more desired gaze areas representing the one or more spectators and
   providing user feedback indicative of the evaluated level of eye-contact to the user,
   wherein the evaluating is also based on a speech pattern of the recorded speech signal, wherein the evaluating comprises evaluating that the user's movement of gaze direction matches a speech pattern of the speech signal.

2. The method according to claim 1, wherein the one or more rules comprises a minimum and/or maximum time the user's gaze direction should constantly remain on a desired gaze area indicated by a user interface object representing one of the spectators.

3. The method according to claim 1, wherein the minimum time corresponds to an estimated time it takes for the user to say at least one sentence.

4. The method according to claim 1, wherein the rules are based on a timing within a speech to be performed by a user.

5. The method according to claim 1, wherein the presenting comprises presenting speech information related to a speech to be performed by the user, and wherein the rules are based on the speech information.

6. The method according to claim 5, wherein the rules are based on phrases or tags in the speech information.

7. The method according to claim 1, wherein the method comprises continually repeating the presenting, the obtaining and the evaluating and providing the user-feedback indicative of the evaluated level of eye-contact to the user in real-time.

8. The method according to claim 1, wherein the one or more user interface objects comprises a plurality user interface objects positioned on distinct parts of the one or more displays and representing individual spectators, and wherein the method comprises moving the desired gaze area between the one or more gaze areas, according to a pre-defined eye contact training pattern.

9. The method according to claim 8, wherein the method comprises:
   continually indicating one spectator of the one or more of the spectators, with whom eye contact should be established and the evaluating comprises evaluating a level of eye contact between the user and the indicated spectator.

10. The method according to claim 1, wherein the one or more user interface objects comprises one single user interface object positioned right below the camera, wherein the single user interface object represents eye-contact via the camera.

11. The method according to claim 1, wherein the evaluating comprises detecting silent periods in the recorded speech and considering the level of eye contact to be "good" upon the user only moving his/her gaze during the detected silent periods.

12. The method according to claim 1,
wherein the method comprises:
moving the desired gaze area in response to a trigger comprising detection of a silent period in the recorded speech signal.

13. The method according to claim 8, wherein the moving of the desired gaze area is performed in response to one or more triggers.

14. The method according to claim 13, wherein the one or more triggers comprises one or more of:
a user input,
expiry of a timer, or
detection of a silent period in a recorded speech signal.

15. The method according to claim 1, wherein the obtaining comprises estimating at least one of pupil centre, eye fixation time, eye glint data, pupil dilation and constriction, blink rates, and corneal reflection.

16. The method according to claim 1, wherein the one or more desired gaze areas are positioned on the one or more displays or outside the one or more displays.

17. The method according to claim 1, wherein the user-feedback comprises a visible, an audible or a tactile signal.

18. A non-transitory computer-readable medium comprising instructions which, when executed by a computing device, cause the computing device to carry out the method according to claim 1.

19. An electronic user device for eye-contact training, the electronic user device comprising a control device, one or more displays and a camera, wherein the control device is configured to:
record a speech signal representing a user's speech,
present, on the one or more displays, one or more user interface objects indicative of one or more desired gaze areas representing one or more spectators of a virtual audience of the user,
obtain, using the camera, eye-gaze data indicative of the user's actual gaze direction,
evaluate a level of eye contact between the user and the virtual audience based on one or more rules defining a level of eye contact, by analysing an extent to which the user's actual gaze direction indicated by the eye-gaze data corresponds to the one or more desired gaze areas and
provide user feedback indicative of the evaluated level of eye-contact to the user
wherein the evaluating is also based on a speech pattern of the recorded speech signal, wherein the evaluating comprises evaluating that the user's movement of gaze direction matches a speech pattern of the speech signal.

20. The electronic user device according to claim 19, wherein the one or more rules comprises a minimum and/or maximum time the user's gaze direction should constantly remain on a gaze area indicated by a user interface object representing one of the spectators.

21. The electronic user device according claim 19, wherein the control device is configured to continually indicate one spectator of the one or more of the spectators, with whom eye contact should be established and to evaluate a level of eye contact between the user and the indicated spectator.

* * * * *